United States Patent [19]

Engert et al.

[11] Patent Number: 5,618,963

[45] Date of Patent: Apr. 8, 1997

[54] PROCESS FOR THE PREPARATION OF STERICALLY HINDERED HYDROXYBENZYLPHOSPHONATES

[75] Inventors: Thomas Engert, Gross-Rohrheim; Hans Stephan; Walter Wolf, both of Bensheim, all of Germany

[73] Assignee: Ciba-Geigy Corporation, Tarrytown, N.Y.

[21] Appl. No.: 493,775

[22] Filed: Jun. 22, 1995

[30] Foreign Application Priority Data

Jun. 28, 1994 [CH] Switzerland ............... 2058/94

[51] Int. Cl.⁶ ....................................... C07F 9/40
[52] U.S. Cl. ............................ 558/122; 558/214
[58] Field of Search ................... 558/122, 214

[56] References Cited

U.S. PATENT DOCUMENTS

| | | | |
|---|---|---|---|
| 3,006,945 | 10/1961 | Goddard et al. | 260/461 |
| 3,155,704 | 11/1964 | Knapp | 260/461 |
| 3,268,630 | 8/1966 | Spivack | 260/968 |
| 3,787,540 | 1/1974 | Schmidt et al. | 260/970 |
| 3,790,648 | 2/1974 | Schmidt et al. | 260/970 |
| 4,263,232 | 4/1981 | Parekh | 260/989 |
| 5,157,141 | 10/1992 | Dubs et al. | 558/122 |
| 5,171,873 | 12/1992 | Kainmuller et al. | 558/122 |

FOREIGN PATENT DOCUMENTS

| | | |
|---|---|---|
| 0434606 | 6/1991 | European Pat. Off. |
| 0507738 | 10/1992 | European Pat. Off. |
| 2312910 | 9/1974 | Germany . |
| 1487609 | 10/1977 | United Kingdom . |

OTHER PUBLICATIONS

Derwent Abstract 73–63841U/43 of DE2312910 (1973).

Derwent Abstract 45359B/24 of SU–A 619–486 (1978).

V. V. Ovchinnikow et al. in Zh. Obshch Khim. 51,999 (1981).

*Primary Examiner*—Joseph McKane
*Assistant Examiner*—Michael G. Ambrose
*Attorney, Agent, or Firm*—Michele A. Kovaleski

[57] ABSTRACT

A process is described for the preparation of hydroxybenzylphosphonates of the formula I

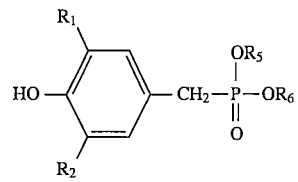

which involves A) reacting a phenol of the formula II

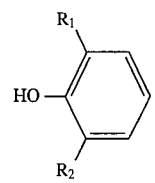

with an amine of the formula III

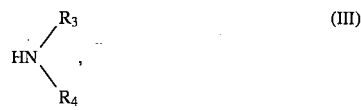

formaldehyde or paraformaldehyde and a protonic acid $H_nA$ to give a salt of the formula IV

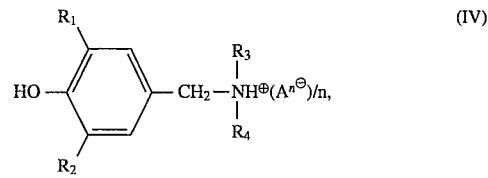

B) distilling off the water of reaction which forms, and C) reacting the reaction mixture, or the salt IV isolated therefrom, with a trialkyl phosphite of the formula

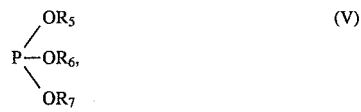

in which $H_nA$ is an organic or inorganic acid having n protons, n is 1, 2, 3 or 4, $R_1$ and $R_2$ independently of one another are $C_1$-$C_{12}$alkyl or $C_5$-$C_7$cycloalkyl, $R_3$ and $R_4$ independently of one another are $C_1$-$C_{12}$alkyl or form, together with the nitrogen atom attached to them, a piperidyl or morpholinyl radical, and $R_5$, $R_6$ and $R_7$ independently of one another are $C_1$-$C_4$alkyl; and the compounds of the formula I are suitable, for example, as processing stabilizers for plastics.

17 Claims, No Drawings

PROCESS FOR THE PREPARATION OF STERICALLY HINDERED HYDROXYBENZYLPHOSPHONATES

The invention relates to a process for the preparation of sterically hindered hydroxybenzylphosphonates and metal salts derived therefrom.

Sterically hindered hydroxybenzylphosphonates are employed, for example, as processing stabilizers for plastics. A range of processes for their preparation are known (see eg. U.S. Pat. No. 3,790,648, U.S. Pat. No. 3,006,945, SU-A 619 486, DE-A 2 222 708, FR-A 1 382 891).

One group of these processes makes use of the reaction with Mannich bases of the formula

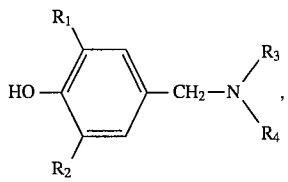

in which the radicals $R_1$ to $R_4$ may, for example, have the definitions described below.

U.S. Pat. No. 3,155,704 and DE-A 2 312 910 describe the quaternization of such Mannich bases with methyl iodide and the reaction of the ammonium salts with trialkyl phosphites. However, methyl iodide is on the one hand relatively expensive and, on the other hand, highly carcinogenic, and consequently it can only be handled subject to strict safety precautions.

According to U.S. Pat. No. 3,790,648, the Mannich bases are reacted, in the presence of alkali metals or their hydrides or amides, with dialkyl phosphites. Owing to the particular sensitivity of starting materials and products in the presence of strong alkalis, the formation of discoloured products occurs and, although this can be avoided by using additives in accordance with U.S. Pat. No. 4,263,232, the yields leave something to be desired. In addition, there is the risk of unwanted hydrolysis of the products.

DE-A 2 456 532 and V. V. Ovchinnikow et al. in Zh. Obshch. Khim. 51, 999 (1981) describe the direct reaction of Mannich bases with, respectively, trialkyl and dialkyl phosphites. One disadvantage of this procedure is the long reaction time.

In addition, DE-A 2 312 910 describes alternatives to the Mannich bases, in which, for example, the amino group is replaced by bromide or acetate. The compounds are isolated prior to the reaction with phosphites and the overall yields are substantially lower than when the corresponding Mannich bases are used.

Furthermore, it is known (EP-A 507 738) that hydroxybenzylphosphonates can be prepared by reacting Mannich bases with trialkyl phosphites in the presence of carboxylic anhydrides.

Moreover, U.S. Pat. No. 5,157,141 discloses a process in which hydroxybenzylphosphonates are obtained in yields of around 80% by reaction of phenol, formaldehyde and amine and direct addition of trialkyl phosphite.

It has now been found that a very much more advantageous overall process arises if a salt of the Mannich base is prepared as intermediate, and the water of reaction is removed between the two stages. By this means, the yield is increased considerably. Isolation or purification of the Mannich base and its salt is not necessary in this process. The process makes use of the following reactions:

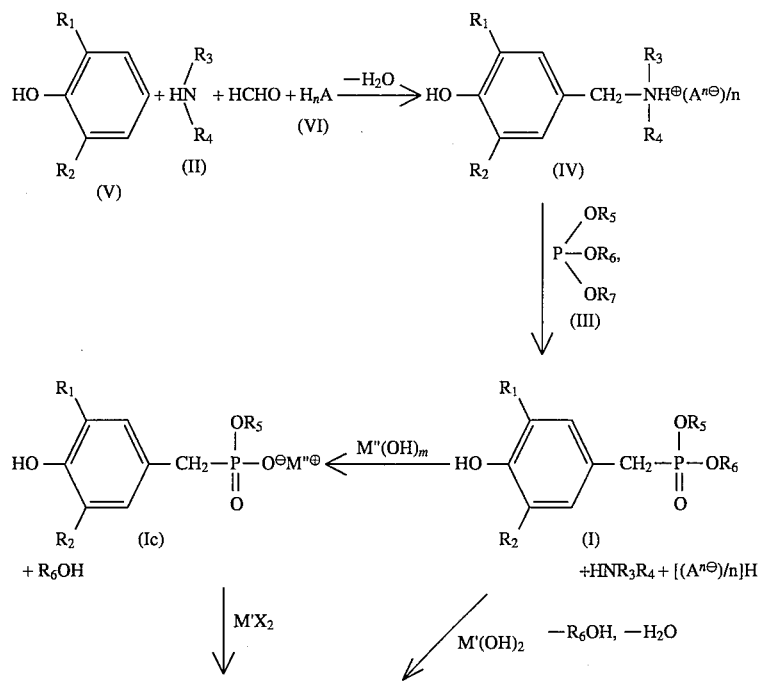

-continued

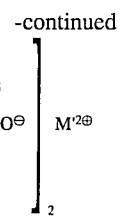

(M' is alkaline earth metal, X is e. g. halogen; M" is ammonium or alkali metal.)

Specifically, the process relates to the preparation of hydroxybenzylphosphonates of the formula I

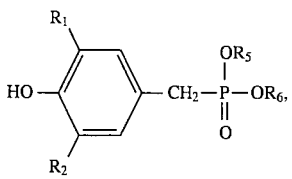 (I)

by
A) reacting a phenol of the formula II

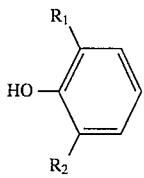 (II)

with an amine of the formula III

 (III)

formaldehyde or paraformaldehyde and a protonic acid $H_nA$ to give a salt of the formula IV

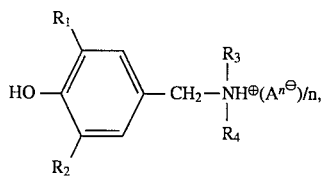 (IV)

B) distilling off the water of reaction which forms, and
C) reacting the reaction mixture, or the salt IV isolated therefrom, with a trialkyl phosphite of the formula

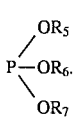 (V)

In these formulae
$H_nA$ is an organic or inorganic acid having n (1, 2, 3 or 4) protons,
$R_1$ and $R_2$ independently of one another are $C_1$-$C_{12}$alkyl or $C_5$-$C_7$cycloalkyl,
$R_3$ and $R_4$ independently of one another are $C_1$-$C_{12}$alkyl or they form, together with the nitrogen atom attached to them, a piperidyl or morpholinyl radical, and
$R_5$, $R_6$ and $R_7$ independently of one another are $C_1$-$C_4$alkyl.

The process can also be used for the preparation of salts of the formula Ia, in which a resulting compound of the formula I

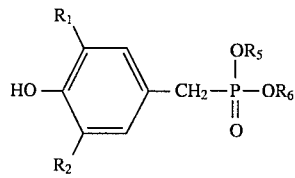 (I)

is reacted (hydrolysed) with a base $M(OH)_m$, in which m is 1 or 2 and M is ammonium, alkali metal or alkaline earth metal, to give a salt of the formula Ia

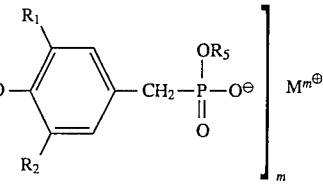 (Ia)

which is, if desired (if M=alkali metal or ammonium and m=1), reacted with a salt of an alkaline earth metal to give a further salt of the formula Ia in which M is an alkaline earth metal and m is 2.

$C_1$-$C_{12}$Alkyl radicals $R_1$, $R_2$, $R_3$ and $R_4$ in the above formulae are branched or unbranched radicals. Examples thereof are methyl, ethyl, propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl. $R_5$, $R_6$ and $R_7$ as $C_1$-$C_4$alkyl are suitably, for example, methyl, ethyl, propyl, isopropyl, n-butyl, isobutyl and t-butyl.

$R_1$ and $R_2$ as $C_5$-$C_7$cycloalkyl can be cyclopentyl, cyclohexyl or cycloheptyl.

Examples of suitable protonic acids $H_nA$ are inorganic or organic acids such as, for example, hydrochloric acid, sulfuric acid, phosphoric acid, methanesulfonic acid, methanephosphonic acid, p-toluenesulfonic acid or carboxylic acids. It is preferred to use acids having from 1 to 3 protons (n=1, 2 or 3).

Suitable carboxylic acids are those which are monovalent, such as acetic acid, propionic acid, butyric acid, valeric acid, pivalic acid, hexanoic acid, oenanthic acid, octanoic acid, neodecanoic acid, 2-ethylhexanoic acid, pelargonic acid, decanoic acid, undecanoic acid, dodecanoic acid, tridecanoic acid, myristic acid, palmitic acid, isostearic acid, stearic acid, 12-hydroxystearic acid, behenic acid, benzoic acid, p-tert-butylbenzoic acid, dimethylhydroxybenzoic acid, 3,5-di-tert-butyl-4-hydroxybenzoic acid, toluic acid, dimethylbenzoic acid, ethylbenzoic acid, n-propylbenzoic acid, salicylic acid, p-tert-octylsalicylic acid, and sorbic acid; those which are rivalent, such as oxalic acid, malonic acid, succinic acid, glutaric acid, adipic acid, fumaric acid, pentane-1,5-dicarboxylic acid, hexane-1,6-dicarboxylic acid, heptane-1,7-dicarboxylic acid, octane-1,8-dicarboxylic acid, phthalic acid, isophthalic acid, terephthalic acid and hydroxyphthalic acid; and the di- or tiesters of tri- or tetravalent carboxylic acids, such as hemimellitic acid, trimellitic acid, pyromellitic acid and citric acid. It is particularly preferred to use lower carboxylic acids, for example of the formula RCO—OH in which R is $C_1$-$C_{12}$alkyl. Examples thereof are acetic acid and pivalic acid.

Step A is advantageously carried out at from 0° to 60° C., preferably with particular care being taken that the temperature does not exceed 60° C. In step A, it is advantageous to add to the phenol at least equimolar quantities of amine, formaldehyde and acid. An excess of up to 20%, in particular up to 10%, of one or more of these reactants can be advantageous.

Step B: Distillation takes place preferably at a constant temperature of not more than 60° C., i.e. a partial vacuum is applied in order to distil off the water. If the reaction is carried out in a solvent, the water of reaction can also be distilled off by an entraining agent or azeotropically. The distillation is preferably carried out under reduced pressure. The pressure may for example be in the range from 5 to 100 tort (from about 7 to 135 mbar).

Step C: The intermediate IV is preferably reacted directly, without isolation and/or without purification, with the phosphite V; in other words, for example after distilling off the water of reaction, an at least equimolar quantity of a trialkyl phosphite is added directly to the resulting mixture. It can also be advantageous in this instance to employ a slight excess, for example from 5 to 20%, in particular 10%, of the phosphite.

In this step C the reaction temperatures are advantageously from room temperature to 150° C.; the reaction is preferably begun at from room temperature to 60° C., and then the temperature is subsequently raised slowly in such a way that the by-products are distilled off. In this part of the process, too, it is possible to apply a partial vacuum in order to distil off any relatively nonvolatile by-products.

Step C can thus be carried out at atmospheric pressure or reduced pressure. If carried out under reduced pressure, this pressure is preferably from 500 to 150 mbar.

Following step C, in a preferred embodiment the by-products are removed by distillation at a temperature of from 100° to 170° C. under a pressure of from 5 to 20 mbar.

The process is preferably carried out without solvent. The presence of an organic solvent, especially an aprotic and preferably a high-boiling solvent, however, may be advantageous. This solvent may be nonpolar or polar. Examples of polar aprotic solvents are dimethylformamide, dimethylacetamide and N-methylpyrrolidone. Examples of preferred solvents are aliphatic hydrocarbons such as heptane, octane, cyclohexane and decalin, mineral oil distillates such as petroleum ether, ligroin and kerosine, aromatic hydrocarbons such as benzene, toluene or xylenes, esters such as ethyl acetate, ethers such as dibutyl ether or tetrahydrofuran, or mixtures of the solvents mentioned. Use is made in particular of high-boiling aliphatic or aromatic solvents.

Among these solvents, particular preference is given to petroleum ether fractions, especially the petroleum ether fractions 100/140 (naphtha benzinc) and 160/200, and to ethyl acetate.

If a solvent is used, it may be used in step A or C or in both steps. In the latter case, it is possible either to employ the same solvent in both steps or a different solvent in each step. In the case of two different solvents, the solvent used in step A is distilled off, wholly or partially, prior to step C, unless the salt of the formula IV is isolated.

The process is employed in particular for the preparation of compounds of the formula I in which $R_1$ and $R_2$ independently of one another are $C_1$-$C_6$alkyl or cyclohexyl. In formula III, $R_3$ and $R_4$ are preferably and independently of one another $C_1$-$C_6$alkyl, or they form, together with the nitrogen atom attached to them, a piperidyl or morpholinyl radical. In formula I, at least one of the radicals $R_1$ and $R_2$ is preferably tert-butyl.

The process is preferably used to prepare compounds of the formula I in which $R_1$ and $R_2$ are tert-butyl radicals.

The salts of the formula Ia are obtained by reaction with a base. Examples of suitable bases $M(OH)_m$ are NaOH, KOH, $Ca(OH)_2$ or aqueous ammonia ("$NH_4OH$"). Aqueous alkalis such as sodium hydroxide or potassium hydroxide are particularly advantageous. By further reactions of compounds of the formula Ia in which m is 1 with alkaline earth metal salts, in particular with alkaline earth metal halides, it is possible to obtain salts of the formula Ia in which M is alkaline earth metal and m is 2.

The hydrolysis step takes place in accordance with methods which are customary in organic chemistry. An advantageous procedure is one in which the compound of the formula I is maintained at a temperature of from 80° to 150° C. with an excess of the aqueous alkali for a number of hours, with pressure being applied if necessary. It is advantageously heated with concentrated alkali under superatmospheric pressure for from about 3 to 5 hours at about 120° C., and in this context the pressure can be different depending on the proportion of solvent. The resulting salt is precipitated, either on cooling or after concentration by evaporation, and can be filtered off in the customary manner or isolated in another way.

Compounds of the formula Ia where M is alkaline earth metal can also be obtained from the alkali metal salts or ammonium salts by, for example, dissolving these salts in water, with heating if necessary, and using an alkaline earth metal halide to form the alkaline earth metal salt of the formula Ia which, after concentration if necessary, precipitates and can be filtered off or can be isolated in some other way. It is preferred to use $CaCl_2$ to form the calcium salt.

The products of the formula I are worked up by conventional methods, such as washing-out of the water-soluble by-products, recrystallization, etc. In general water is added to the reaction mixture in order to remove water-soluble reaction products. When this is done, or after removal of the water from the reaction mixture, the desired product is precipitated. It can then be filtered off with suction and washed with the solvent used.

The compounds of the formulae I and Ia prepared by the process according to the invention are suitable as stabilizers for a large number of organic monomers and polymers against thermal, oxidative and/or light-induced degradation, as described, for example, in U.S. Pat. No. 3,280,070, U.S. Pat. No. 3,281,505 and U.S. Pat. No. 3,367,870.

The examples which follow illustrate the invention further without limiting it. As in the remainder of the description and unless stated otherwise, parts and percentages are by weight.

Example 1

63 g of paraformaldehyde (2.1 mol), 120.1 g of glacial acetic acid (2.0 mol) and 412.7 g of 2,6-di-tert-butylphenol (2.0 mol) are placed as initial charge in a reaction vessel with stirrer, thermometer, condenser, dropping funnel and inert gas blanketing. Beginning at 300 mbar and at a temperature of 20° C., 94.7 g (2.1 mol) of dimethylamine are introduced below the level of the starting materials over the course of 20 minutes, during which the temperature rises to 53° C. The mixture is subsequently heated to 60° C. and stirred at this temperature for 30 min and, again beginning at 300 mbar, the water of reaction is distilled off over 2 h. At the end of the distillation, the pressure is 100 mbar and the temperature is 85° C.

372 g (2.24 mol) of triethyl phosphite are added at 50° C. to the 640 g of Mannich base salt obtained in this way, and the mixture is heated to 83° C. over the course of 45 min with stirring. It is then heated to 130° C. and maintained at this temperature for 3 h, during which the by-products which form are distilled off at from 200 to 150 mbar. 300 ml of petroleum ether 100/140 are added and the mixture is divided into two portions which are washed with a total of 500 ml of water. The product crystallizes out on cooling to room temperature, and is filtered off with suction and washed with a little petroleum ether 100/140. The product is dried to give 665 g (93.3% of theory) of diethyl 4-hydroxy-3,5-di-ten-butylbenzylphosphonate as a colourless product in a purity of 99.9%. m.p.: 119°–121° C.

Example 2

17.2 g of paraformaldehyde (0.573 mol), 38.7 g of glacial acetic acid (0.644 mol) and 103.2 g of 2,6-di-tert-butylphenol (0.5 mol) are placed at room temperature as initial charge in a reaction vessel with stirrer, thermometer, condenser, dropping funnel and inert gas blanketing, and 51.9 g (0.61 mol) of pyridine are added. The mixture is heated at 60°–64° C. for 45 minutes. The water of reaction is distilled off at 300 mbar and 77° C.

After the mixture has cooled, the Mannich base salt is obtained in the form of pale crystals.

The salt is reacted with triethyl phosphite as above in Example 1 and worked up in the same way.

Example 3

31.52 g of paraformaldehyde (1.05 mol), 102.1 g of pivalic acid (1.0 mol) and 206.3 g of 2,6-di-tert-butylphenol (1 mol) are placed at room temperature as initial charge in a reaction vessel with stirrer, thermometer, condenser, dropping funnel and inert gas blanketing. 47.3 g (1.05 mol) of dimethylamine are introduced below the level of the starting materials at 10° C. over the course of 12 minutes, during which the temperature rises to 40° C. The mixture is subsequently heated to 60° C., stirred at this temperature for 20 min, and the water of reaction is distilled off at 200 mbar and 80° C.

186 g (1.12 mol) of triethyl phosphite are added to the resulting reaction mixture at room temperature, and the mixture is heated at 95° C. with stirring until a solution has formed. The by-products which form are subsequently distilled off at 150 mbar and 120° C. After 3 h, petroleum ether 100/140 is added. The product crystallizes out on cooling to room temperature, and is filtered off with suction and washed with a little petroleum ether 100/140. The product is dried to give 296.3 g (83.1% of theory) of diethyl 4-hydroxy-3,5-di-tert-butylbenzylphosphonate as a colourless product in a purity of >99%. m.p.: 119°–121° C.

Example 4

35.3 g of 89.3% paraformaldehyde (1.05 mol), 61.3 g of glacial acetic acid (1.02 mol) and 100 g of a high-boiling nonaromatic petroleum spirit (boiling range 160° to 200° C.) are placed at room temperature as initial charge in a reaction vessel with stirrer, thermometer, condenser, dropping funnel and inert gas blanketing. The reaction vessel is evacuated, and 43.3 g of dimethylamine (1.05 mol) are added above the level of the starting materials over the course of about 10 min at a temperature of 20° C., which rises slowly to 43° C., and at a pressure of 328 mbar, which rises to 532 mbar. The mixture is then heated to 50° C., and 206.3 g (1 mol) of 2,6-di-tert-butylphenol are added. The reaction mixture is heated to 93° C. and the water of reaction is distilled off while the pressure drops from 436 to 250 mbar.

186.1 g of triethyl phosphite are then added dropwise at 900 mbar and at from 82° to 75° C., and the mixture is stirred at from 75 to 77° C. and, at 400 mbar, heated to 107° C. At a bottom temperature of from 107° to 153° C. and under a pressure of from 400 to 15 mbar, the volatile by-products are subsequently distilled off, a further 250 g of the high-boiling petroleum spirit are added, and the mixture is slowly cooled to 20° C. The product crystallizes, and is filtered off with suction, washed with a little solvent and dried.

Yield 336.0 g (94% of theory) of diethyl 4-hydroxy-3,5-di-tert-butylbenzylphosphonate.

What is claimed is:

1. A process for the preparation of a hydroxybenzylphosphonate of the formula (I)

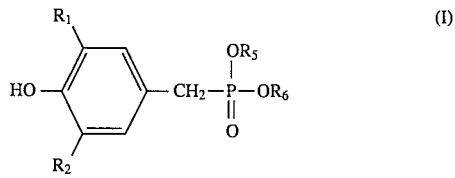

which comprises

A) reacting a phenol of the formula II

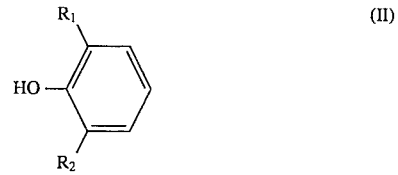

with an amine of the formula III

formaldehyde or paraformaldehyde and a protonic acid $H_nA$ to give a salt of the formula IV

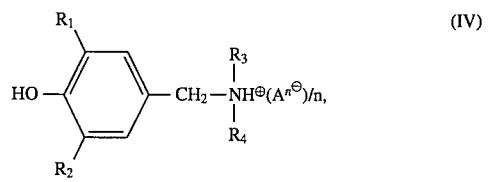

B) distilling off the water of reaction which forms, and

C) reacting the reaction mixture, or the salt IV isolated therefrom, with a trialkyl phosphite of the formula

in which $H_nA$ is an organic or inorganic acid having n protons, n is 1, 2, 3 or 4, $R_1$ and $R_2$ independently of one another are $C_1$-$C_{12}$alkyl or $C_5$-$C_7$cycloalkyl, $R_3$ and $R_4$ independently of one another are $C_1$-$C_{12}$alkyl or form, together with the nitrogen atom attached to them, a piperidyl or morpholinyl radical, and $R_5$, $R_6$ and $R_7$ independently of one another are $C_1$-$C_4$alkyl.

2. A process according to claim 1, wherein a resulting compound of the formula I

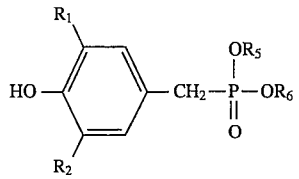

is reacted with a base $M(OH)_m$ to give a salt of the formula Ia

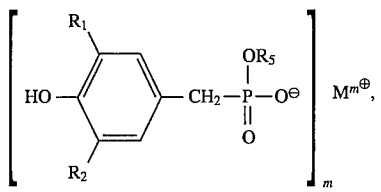

in which M is ammonium, alkali metal or alkaline earth metal and m is 1 or 2.

3. A process according to claim 2, wherein a resulting compound of the formula Ia

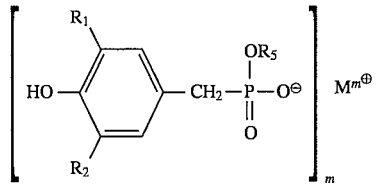

in which M is alkali metal or ammonium is reacted with alkaline earth metal salt to give a further salt of the formula Ia in which m is 2 and M is alkaline earth metal.

4. A process according to claim 1, wherein $H_nA$ is a carboxylic acid RCO—OH in which R is $C_1$-$C_{12}$alkyl.

5. A process according to claim 4, wherein the by-products which form in stage C, $HNR_3R_4$ and RCO—$OR_7$, are removed by distillation.

6. A process according to claim 1, wherein $R_1$ and $R_2$ independently of one another are $C_1$-$C_6$alkyl or cyclohexyl, and $R_3$ and $R_4$ independently of one another are $C_1$-$C_6$alkyl or form, together with the nitrogen atom attached to them, a piperidyl or morpholinyl radical.

7. A process according to claim 1, wherein $R_1$ and $R_2$ are tert-butyl radicals.

8. A process according to claim 1, wherein the reaction temperature in step A is from 0° to 60° C.

9. A process according to claim 8, wherein the reaction temperature in step A is from 30° to 60° C.

10. A process according to claim 1, wherein the reaction temperature in step C is from 100° to 140° C.

11. A process according to claim 1, which is carried out without solvent.

12. A process according to claim 1, wherein step A and/or step C are carried out in a solvent.

13. A process according to claim 1, wherein the reactions are carried out in a high-boiling solvent.

14. A process according to claim 1, wherein the reactions are carried out in a high-boiling aliphatic or aromatic solvent.

15. A process according to claim 1, wherein step C is carried out at atmospheric pressure or reduced pressure.

16. A process according to claim 1, wherein the pressure in step C is from 500 to 150 mbar.

17. A process according to claim 1, wherein after step C the by-products are removed by distillation at a temperature of from 100° to 170° C. under a pressure of from 5 to 20 mbar.

* * * * *